(12) United States Patent
Koellhofer et al.

(10) Patent No.: US 8,439,193 B2
(45) Date of Patent: May 14, 2013

(54) MEDICAL GUIDEWIRE BASIN

(75) Inventors: David B Koellhofer, Verona, NJ (US);
Mitchell R Weaver, Bloomfield Hills, MI (US)

(73) Assignee: MD Vascular International, LLC, Chicago, IL (US)

( * ) Notice: Subject to any disclaimer, the term of this patent is extended or adjusted under 35 U.S.C. 154(b) by 0 days.

(21) Appl. No.: 13/487,943

(22) Filed: Jun. 4, 2012

(65) Prior Publication Data

US 2012/0312703 A1 Dec. 13, 2012

Related U.S. Application Data

(60) Provisional application No. 61/496,373, filed on Jun. 13, 2011.

(51) Int. Cl.
*B65D 83/10* (2006.01)
*A61B 5/00* (2006.01)

(52) U.S. Cl.
USPC .................. 206/370; 242/588.6; 134/117

(58) Field of Classification Search ............... 242/588.6, 242/400.1; 206/363, 370, 438, 210, 207, 206/205; 134/117
See application file for complete search history.

(56) References Cited

U.S. PATENT DOCUMENTS

| | | | | |
|---|---|---|---|---|
| 4,282,972 A | * | 8/1981 | Chiulli | 206/303 |
| 5,125,416 A | * | 6/1992 | Phillips | 600/585 |
| 5,611,428 A | | 3/1997 | Banerian | |
| 5,738,213 A | * | 4/1998 | Whiting et al. | 206/364 |
| 5,769,222 A | | 6/1998 | Banerian | |
| D433,130 S | | 10/2000 | Cude | |
| 6,547,072 B2 | * | 4/2003 | Whiting et al. | 206/364 |
| 6,569,106 B1 | | 5/2003 | Ullman | |
| 6,691,946 B2 | * | 2/2004 | Dannecker et al. | 242/588.6 |
| 6,802,323 B1 | | 10/2004 | Truwit | |
| 7,766,162 B2 | * | 8/2010 | Maki et al. | 206/364 |
| 2004/0255991 A1 | | 12/2004 | Truwit | |
| 2010/0170816 A1 | | 7/2010 | Burgess | |

FOREIGN PATENT DOCUMENTS

WO WO 9856687 A1 12/1998
WO WO 02087996 A1 11/2002

* cited by examiner

*Primary Examiner* — Jacob K Ackun
(74) *Attorney, Agent, or Firm* — Gearhart Law, LLC

(57) ABSTRACT

A novel container for storing medical guidewires in liquid is disclosed herein. The container comprises a substantially rectangular basin where the guidewire coils are separated horizontally into individual bays. Specific tabs and dividers hold the coils in place and keep the wires untangled. The horizontal placement of the wires enables a clinician to instantly differentiate between wires, select the right coil without spending time in untangling wires and allows storing of the wires is relatively small amount of storing liquid.

13 Claims, 5 Drawing Sheets

MEDICAL GUIDEWIRE BASIN

PRIORITY

This application claims priority of provisional application No. 61/496,373 filed on Jun. 13, 2011 and incorporated herein in its entirety by reference.

FIELD OF THE INVENTION

The invention relates to medical devices and containers to store medical devices during medical procedures.

BACKGROUND OF THE INVENTION

The present invention relates to medical devices, in particular, the present invention relates to a container for storing medical guidewires and catheters in solution during medical procedures.

Medical guidewires are utilized during endoluminal catheterization procedures typically performed by interventional cardiologists, interventional radiologists and vascular surgeons.

Multiple and different types of guidewires are often required during a single procedure. Typically, the same guidewire may be needed more than once during a medical procedure and therefore it is practical and economical to store the guidewires in specific solution during the procedure.

Typical length of a guidewire is 31.5 to 118.1 inches (80 to 300 cm); most commonly used are 70.9 inches (180 cm) and 102.4 inches (260 cm) long. Typical diameter of guidewire is between 0.014 to 0.0040 inches. When the guidewire is coiled up a typical coil diameter is between 7.1 and 11.0 inches (18 and 28 cm, respectively). Due to the length and the extremely small diameter of the guidewires, handling of these devices during medical procedures may be difficult. Moreover, guidewires are made of material that by its nature resists coiling. If the guidewire-coil is not properly stored the guidewire may rapidly uncoil and the up shooting end of the wire may cause injury and the wire may get contaminated.

Moreover, the wires get easily tangled, and untangling the wires increases risk of contamination. It may be difficult to differentiate between the guidewires if they get tangled. Moreover, a medical procedure most often requires fast action and clearing a tangled guidewire creates unnecessary waste of time.

Yet another problem with the currently existing guidewire containers is that the guidewires are stored in liquid and if each guidewire is stored in separate container the amount of storage solution becomes large. Also having each guidewire in separate container creates a problem in operation rooms where available surface space is limited.

A further problem with currently available containers is that loading of the guidewires into the container is difficult and slow.

There are several containers currently available for storing guidewires. The containers known so far are circular or ovoid shape so as to prevent the guidewire coils from opening. However, none of these solve the problems indicated above.

U.S. Pat. Nos. 6,691,946 and 6,547,072 disclose a medical bowl for a coiled guidewire. These devices are meant to help to keep the guidewire in a coil. The bowls allow storing a single guidewire in a single bowl. The idea of stacking a multitude of bowls on top of each other to save surface space in the operation room is disclosed.

Similarly, U.S. Patent Application Publication U.S. 2010/017816 discloses a bowl with retention devices to hold a single coiled guidewire in a single bowl.

U.S. Pat. No. 5,125,416 discloses a container for medical guidewires where several wires can be stored in one container. However, handling of the wires in this container is not easy, loading the wires into the container is slow and difficult, and distinguishing between the wires is also difficult because only the end of the wires remain visible.

Accordingly, there is a need for a novel container to store medical guidewires in solution during medical procedures which overcomes the problems described above.

SUMMARY OF THE INVENTION

It is an object of this invention to provide a container where multiple guidewires can be stored in liquid simultaneously without getting the wires tangled.

It is another object of this invention to provide a container that allows clinicians to easily identify the guidewire that is needed at any time.

Yet another object of this invention is to provide a container that allows fast retrieval of desired guidewire.

Another object of this invention is to provide a container that allows fast loading of desired guidewire.

Still another object of this invention is to provide a container where guidewires are separated horizontally and are easily visible.

A further object of this invention is to provide a container to store guidewires in relatively small liquid amount.

Still another object of this invention is to provide a rectangular container for storing guidewires in liquid.

This invention provides a container for storing in liquid a multitude of medical guidewires separated horizontally from each other, said container comprising:
  a substantially rectangular basin having a substantially planar bottom connected to a first and a second end wall and to two side walls with a juncture;
  at least two center dividers and optionally a first and a second end tabs attached in a linear arrangement on the bottom along a central axis of the basin,
  said at least two center dividers and said optional end tabs extending upward from the bottom and said center dividers horizontally separating at least one bay in the basin;
  said optional end tabs comprising a vertical portion, and the vertical portion of the first end tab being attached to the first end wall, and the vertical portion of the second end tab being attached to the second end wall, and the vertical portions having an upper end and a lower end;
    said upper end being attached to a substantially horizontal lip pointing toward center of the basin,
    said lower end being attached to a triangular portion, said triangular portion having two sides aligned with the juncture formed by the end wall and the bottom of the basin, and a third side forming an incline from the bottom toward the vertical portion;
  said center dividers comprising a vertical portion having an upper end and a lower end,
    said upper end being attached to a substantially horizontal lip extending toward the first and the second end wall, whereby the vertical portion and the lip portion form a T-shape,
    said lower end being attached to a triangular portion, said triangular portion having its base along the bottom of the basin and two sides forming inclines from the bottom toward the vertical portion;

wherein the at least one bay is suitable for storing at least a single guidewire by coiling the guidewire between an end tab and a center divider or between two center dividers and secure the guidewire under the horizontal lips to prevent the guidewire from rising up and uncoiling.

One embodiment of this invention is illustrated in the accompanying drawings and will be described in more detail herein below.

DESCRIPTION OF THE PREFERRED EMBODIMENTS

Figure 1:
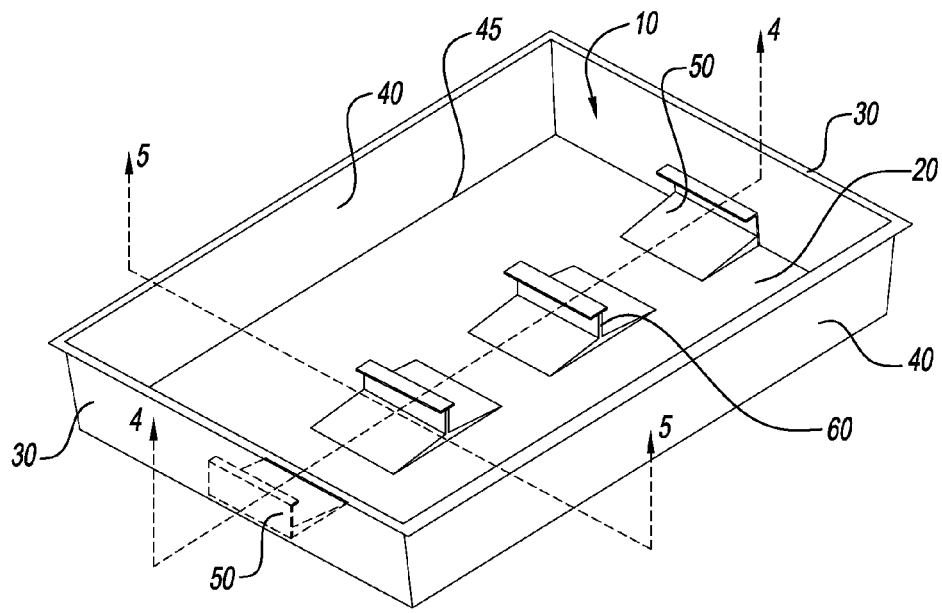
FIG. 1 is a perspective view of a preferred embodiment.

The preferred embodiments of the present invention will now be described with reference to FIGS. 1-9 of the drawings. Identical elements in the various figures are identified with the same reference numerals.

Referring now to FIG. 1, a perspective view of a preferred embodiment of the container is provided. In FIG. 1, the substantially rectangular basin is shown generally as 10, and it comprises a substantially planar bottom 20, two end walls 30 and two side walls 40. The end walls and the side walls are connected to the bottom with a juncture 45 preferably in an angle of 90 degrees or more. Attached or molded into the bottom preferably along the longitudinal axis of the basin are two optional end tabs 50 and at least two center dividers 60. The preferred embodiment comprises two end tabs 50, as is shown in FIG. 1. According to a preferred embodiment the longitudinal axis is a central longitudinal axis, i.e. equally distant from both of the side walls. The end tabs and center dividers are located at an equal distance from both of the side walls. The end tabs are located at close proximity to the end walls and in preferred embodiment they are attached to the end walls.

Figure 2:
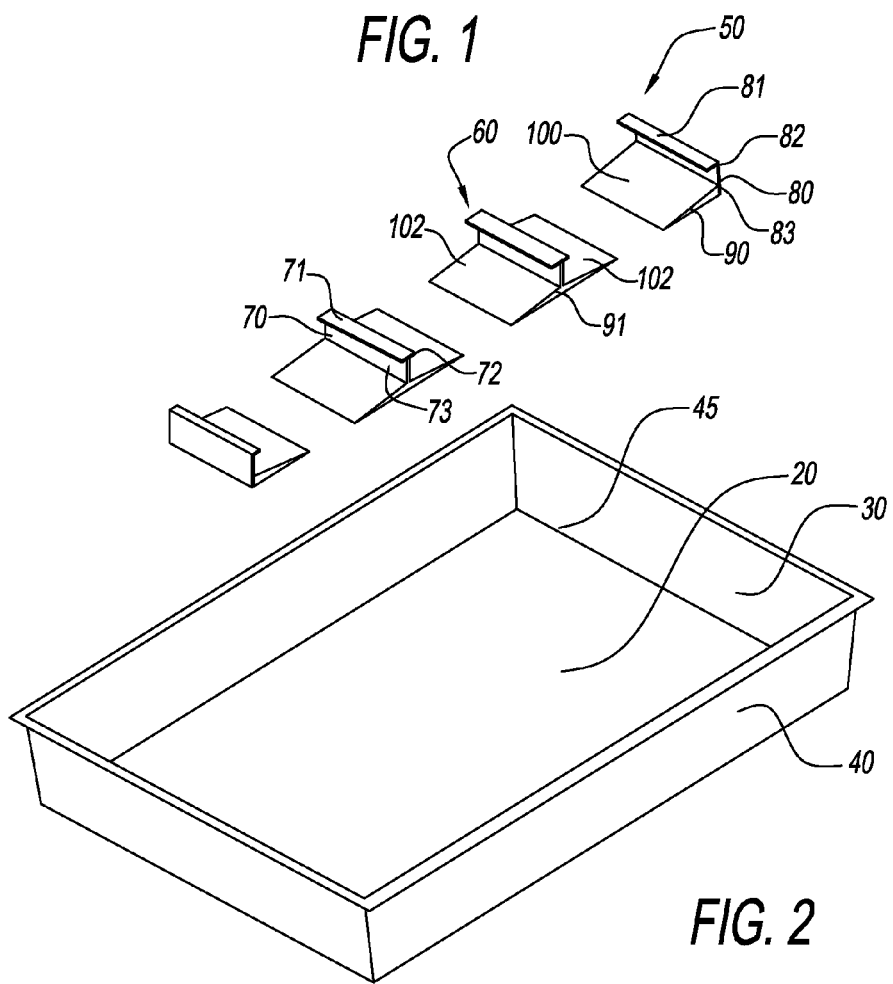
FIG. 2 is an exploded perspective of a preferred embodiment.

Referring now to FIG. 2, a top exploded view of an embodiment of the guidewire basin is provided. The end tabs 50 and the center dividers 60 are shown separately. Each of the end tabs comprises a vertical portion 80 having an upper end 82 and a lower end 83, a horizontal lip 81 attached to the upper end 82 and a triangular portion 90 attached to the lower end 83. The vertical portion 80 of each of the end tabs is preferably attached to one of the end walls 30. The horizontal lips 81 of the end tabs point toward the center of the basin. In one preferred embodiment the triangular portion of the end tabs is a right triangle and the sides forming the right angle are aligned along the right angle formed by right angle juncture 45 of the end wall and the bottom of the basin, whereby the third side 100 of the triangle forms an incline from the bottom toward the end wall. In another preferred embodiment the juncture 45 of the end wall and the bottom of the basin is wider than a right angle and the triangular portion of the end tabs is an obtuse triangle. While the incline 100 is preferably flat as is shown in the drawings, it may also be slightly concave or convex. The surface can be any shape as long as it supports the guidewire coil in a horizontal position above the bottom.

Still referring to FIG. 2, the center dividers 60 comprise a vertical portion 70 having an upper end 72 and a lower end 73, a horizontal lip 71 attached to the upper end and a triangular portion 91 attached to the lower end. The horizontal lip extends horizontally toward both of the end walls, whereby the horizontal lip portion and the vertical portion form a T-shape. The triangular portion is preferably an isosceles triangle having its base along the bottom of the basin, the lower end of the vertical portion being attached to a top of the triangle, whereby two sides of the triangle form inclines 102 from the bottom toward the vertical portion 70. Alternatively, the triangular portion is formed of two right triangles and the lower end of the vertical portion extends to the bottom of the basin and it is secured between the two right triangles.

Figure 3:
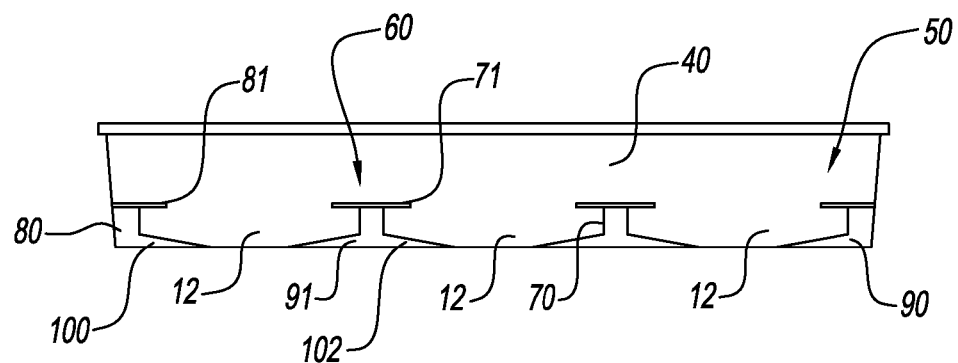
FIG. 3 is a side sectional view of a preferred embodiment along the line 4-4 in FIG. 1.

Now referring to FIG. 3 which provides a sectional view of the basin along the line 4-4 in FIG. 1. The center dividers 60 horizontally separate individual bays 12 in the basin for storing the guidewires. The end tabs 50 and center dividers 60 comprising the vertical portion (70,80), horizontal lip (71,81) and triangular portion (90,91) form a C-shaped channel to keep the guidewire coils intact. The horizontal lips 71, 81 secure the guidewires and prevent the guidewires from rising up and rapidly uncoiling. The inclines 100 and 102 formed by the triangular portions 90, 91 keep the guidewires lifted up from the planar bottom 20 of the basin thereby making handling of the wires easier.

Figure 4:
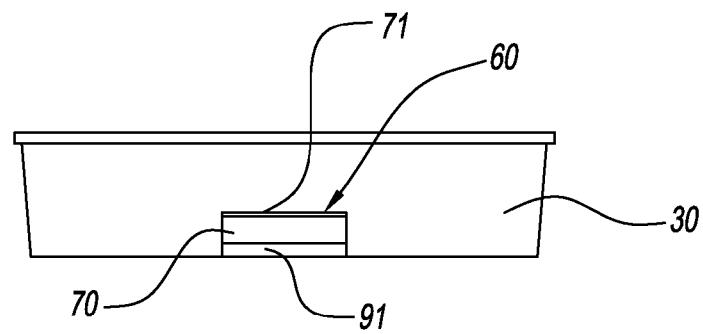
FIG. 4 is a side sectional view of a preferred embodiment along the line 5-5 in FIG. 1.

Now referring to FIG. 4, which provides a sectional view of the basin along the line 5-5 in FIG. 1. The view of the center divider 60 of a preferred embodiment shows that the width of the lip 71, the vertical portion 70 and the triangular portion 91 is substantially the same.

Figure 5:
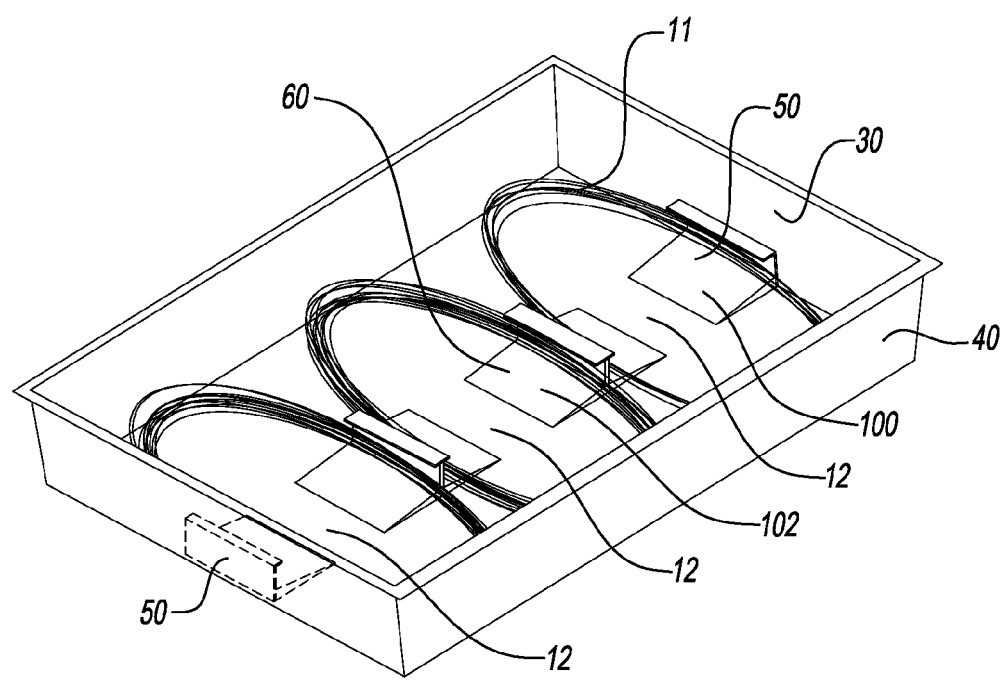
FIG. 5 is a perspective view of a preferred embodiment where the container holds three guidewires.

A preferred embodiment of the container as shown in FIG. 5 holds three coiled guidewires 11. The coiled guidewires are separated from each other horizontally by the center dividers 60 locating between the two end tabs 50 said dividers and tabs locating along the central longitudinal axis. The guidewires are coiled between an end tab and a center divider or between two center dividers and the guidewires are secured under the lips of the dividers and/or tabs to prevent the guidewires from rising up and getting uncoiled and tangled. The guidewire coils located in the bays 12 are separated by the center dividers 60 and once the basin is filled with storing liquid the coils stay uncontaminated in the liquid. The inclines 100 and 102 formed by the triangular portions keep the coils lifted up from the bottom and thereby help handling of the coiled wires. The dimensions of the basin and the number of the center dividers can be modified so that the basin can hold any number of coiled guidewires.

Figure 6:
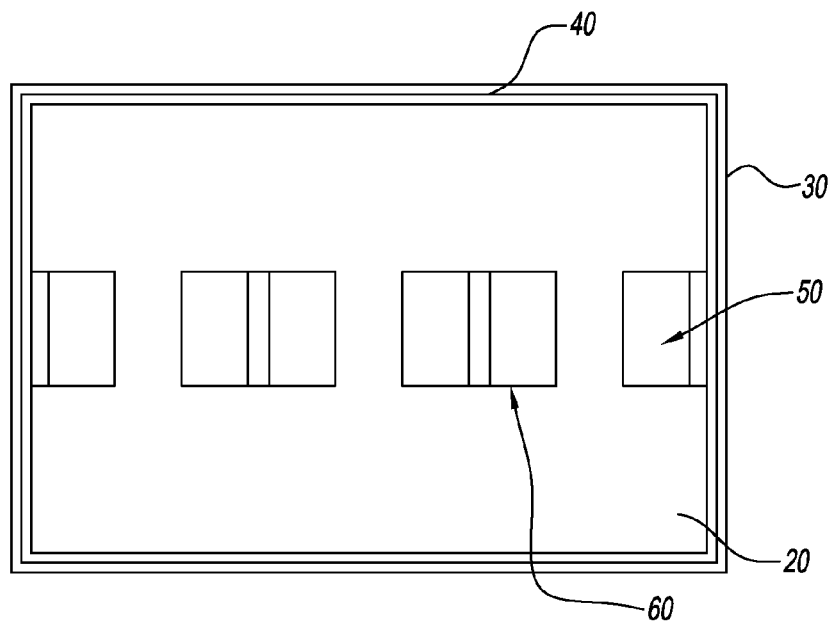
FIG. 6 is a top view of a preferred embodiment.
Figure 7:
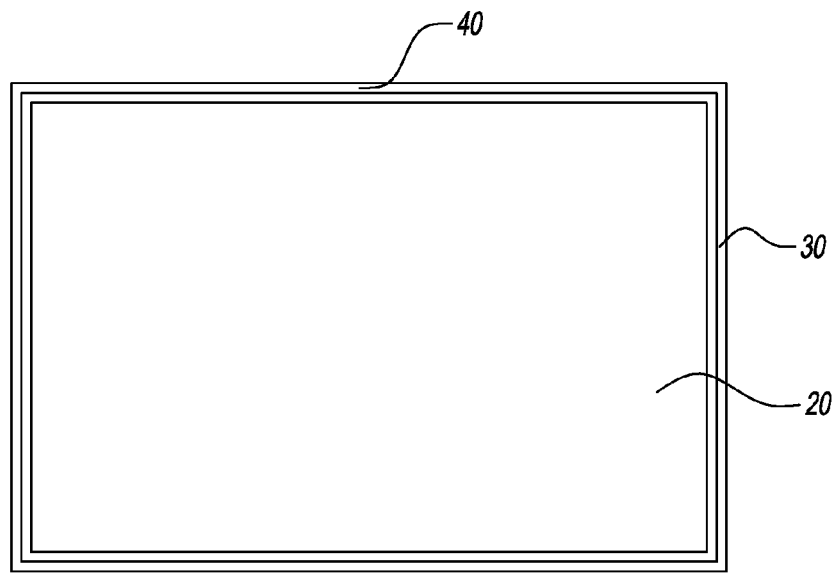
FIG. 7 is a bottom view of a preferred embodiment.
Figure 8:
FIG. 8 is a side view of the long side of a preferred embodiment.
Figure 9:
FIG. 9 is a side view of the short end side of a preferred embodiment.

FIG. 6 shows a top view of the container and FIG. 7 shows the bottom view of the container. FIGS. 8 and 9 show the side view of the side wall 40 and the end wall 30, respectively.

According to a preferred embodiment of this invention, the guidewires are separated horizontally from each other by the center dividers 60. This allows placement of several guidewires in one basin. Furthermore, this allows an easy view to each guidewire individually which is enormously helpful during a medical procedure when a clinician has to quickly choose the right guidewire. Moreover, the invention according to this disclosure allows use of relatively small amount of storage liquid because the wires are stored horizontally in relatively shallow basin.

According to a preferred embodiment of this invention, the depth of the basin is about 2 to 5 inches (5.08 to 12.7 cm) and most preferably about 3 inches (7.62 cm) and the height of the tabs and dividers is about 0.5 to 2 inches (1.27-5.08 cm) and most preferably 1 inch (2.54 cm). According to a preferred embodiment one basin has three bays and accordingly the basin holds three guidewires separated horizontally by the center dividers. The length of such basin is preferentially about 17 to 24 inches (43.18 to 60.69 cm) and most preferably 19 inches (48.26 cm) and the dividers separate bays that are about 5 to 8 inches (12.70 to 20.32 cm) and most preferably 5.8 inches (14.73 cm) wide. The preferred width of a basin is 10-16 inches (25.4-40.64 cm), most preferably 13 inches (33.02 cm). However, the basin can be made in various sizes and one basin may contain any convenient number of bays separated by the dividers.

According to a preferred embodiment the basin is made of polypropylene, but one skilled in the art understands that other materials can also be used. According to one preferred embodiment the basin including the dividers is molded in one piece. According to another embodiment the dividers may be manufactured separately from the basin and the attached to the bottom.

According to one preferred embodiment the basin is stackable and several basins can be stacked on top of each other. The basin according to this invention may be disposable or it may be reusable.

Although this invention has been described with a certain degree of particularity, it is to be understood that the present disclosure has been made only by way of illustration and that numerous changes in the details of construction and arrangement of parts may be resorted to without departing from the spirit and the scope of the invention.

We claim:

1. A container for storing in liquid a multitude of medical guidewires separated horizontally from each other, said container comprising:
    a substantially rectangular basin having a substantially planar bottom connected with two side walls and to a first and a second end wall with a juncture forming an angle of at least 90 degrees;
    a first and a second end tab and at least two center dividers attached in a linear arrangement on the bottom along a central longitudinal axis of the basin,
    said end tabs and center dividers extending upward from the bottom and said center dividers horizontally separating multiple bays in the basin;
    said end tabs comprising a vertical portion and the vertical portion of the first end tab being attached to the first end wall, and the vertical portion of the second end tab being attached to the second end wall, and the vertical portion having an upper end and a lower end;
        said upper end being attached to a substantially horizontal lip pointing toward center of the basin,
        said lower end being attached to a triangular portion, said triangular portion having two sides forming an angle of at least 90 degrees and being aligned with the juncture formed by the end wall and the bottom of the basin and a third side forming an incline from the bottom toward the vertical portion;
    said center dividers comprising a vertical portion having an upper end and a lower end,
        said upper end being attached to a substantially horizontal lip extending toward the first and the second end wall, whereby the vertical portion and the lip form a T-shape,
        said lower end being attached to a triangular portion, said triangular portion having its base along the bottom of the basin and two sides forming inclines from the bottom toward the vertical portion;
            wherein each bay is suitable for storing a single guidewire by coiling the guidewire between an end tab and a center divider or between two center dividers and securing the guidewire under the horizontal lips to prevent the guidewire from rising up and uncoiling.

2. The container of claim 1, wherein the triangular portion of the center divider is formed of two right angle triangles, and wherein the lower end of the vertical portion is secured in between the two right angle triangles.

3. The container of claim 1, wherein the basin has two central dividers, whereby the basin has three bays horizontally separated by the central dividers.

4. The container of claim 1, wherein the juncture is a right angle juncture and the triangular portion of the end tabs has two sides forming a right angle aligned with the juncture.

5. The container of claim 1, wherein the juncture is an angle larger than right angle and the triangular portion of the end tabs is an obtuse triangle having two sides aligned with the juncture.

6. The container of claim 1, wherein the basin is 2-5 inches high, the dividers and tabs about 0.5-2 inches high, the side walls are about 17-24 inches long and the end walls about 10-16 inches wide.

7. The container of claim 1, wherein the bays are about 5 to 8 inches wide.

8. The container of claim 1, wherein the basin is made of polypropylene.

9. The container of claim 1, wherein the dividers and the tabs are manufactured separately and attached to the basin separately.

10. The container of claim 1, wherein the container is manufactured in one piece.

11. The container of claim 1, wherein the container is stackable.

12. The basin of claim 1, wherein the container is reusable.

13. The basin of claim 1, wherein the container is disposable.

* * * * *